United States Patent
Yamada et al.

(10) Patent No.: US 9,370,185 B2
(45) Date of Patent: Jun. 21, 2016

(54) HERBICIDAL COMPOSITION

(75) Inventors: Ryu Yamada, Shiga (JP); Hiroyuki Okamoto, Shiga (JP); Takashi Terada, Shiga (JP)

(73) Assignee: ISHIHARA SANGYO KAISHA, LTD., Osaka (JP)

( * ) Notice: Subject to any disclaimer, the term of this patent is extended or adjusted under 35 U.S.C. 154(b) by 44 days.

(21) Appl. No.: 14/127,685

(22) PCT Filed: Jun. 22, 2012

(86) PCT No.: PCT/JP2012/066629
§ 371 (c)(1),
(2), (4) Date: Mar. 18, 2014

(87) PCT Pub. No.: WO2012/176938
PCT Pub. Date: Dec. 27, 2012

(65) Prior Publication Data
US 2014/0228217 A1    Aug. 14, 2014

(30) Foreign Application Priority Data
Jun. 24, 2011 (JP) ................................ 2011-140452

(51) Int. Cl.
*A01N 47/36* (2006.01)
*A01N 43/80* (2006.01)

(52) U.S. Cl.
CPC ................ *A01N 47/36* (2013.01); *A01N 43/80* (2013.01)

(58) Field of Classification Search
CPC ............................... A01N 47/36; A01N 43/80
See application file for complete search history.

(56) References Cited

U.S. PATENT DOCUMENTS

| | | |
|---|---|---|
| 2008/0153704 A1 | 6/2008 | Yamaji et al. |
| 2011/0015067 A1 | 1/2011 | Sievernich et al. |

FOREIGN PATENT DOCUMENTS

| | | |
|---|---|---|
| CN | 102065692 A | 5/2011 |
| WO | 2004/014138 A1 | 2/2004 |
| WO | 2005/104848 A1 | 11/2005 |
| WO | 2008/075743 A1 | 6/2008 |
| WO | 2009/112454 A2 | 9/2009 |

OTHER PUBLICATIONS

Rummens, F.H.A., "An improved definition of synergistic and antagonistic effects," Weed Science, vol. 23(1), 4-6 (1975).*
Colby, S.R., Calculating synergistic and antagonistic responses of herbicide combinations, Weeds, vol. 15, 20-22 (1967).*
Richer, D.L., "Synergism—a patent view," Pesticide Science, vol. 19(4), 309-315 (1987).*
Chinese Office Action issued with respect to application No. 201280039474.6, mail date is Sep. 5, 2014.
Search Report from International Application No. PCT/JP2012/066629, mail date is Oct. 17, 2012.
Tanetani et al., "Pesticide Biochemistry and Physiology", vol. 95, No. 1, p. 47-55 (2009).
Japanese Office Action issued in JP Patent Appl. No. 2012-134203, mailed Dec. 22, 2015, along with an English-language translation.

* cited by examiner

*Primary Examiner* — John Pak
(74) *Attorney, Agent, or Firm* — Greenblum & Bernstein, P.L.C.

(57) ABSTRACT

At present, a large number of herbicidal compositions have been developed and used. However, weeds to be controlled include a lot of kinds, and the emergence thereof extends over a long period of time. Therefore, the appearance of a herbicidal composition having a broad weed spectrum and having a high activity and a long residual effect is desired. The present invention relates to a synergistic herbicidal composition comprising (A) at least one member selected from the group consisting of flazasulfuron, nicosulfuron, and their salts and (B) pyroxasulfone or its salt. According to the synergistic herbicidal composition of the present invention, a herbicidal composition having a broad weed spectrum and having a high activity and a long residual effect can be provided.

4 Claims, No Drawings

HERBICIDAL COMPOSITION

TECHNICAL FIELD

The present invention relates to a synergistic herbicidal composition comprising (A) at least one member selected from the group consisting of flazasulfuron, nicosulfuron, and their salts and (B) pyroxasulfone or its salt.

BACKGROUND ART

In order to control undesirable plants in agricultural fields or non-agricultural fields (hereinafter simply referred to as "weeds"), a large number of herbicidal compositions are studied. For example, PTL 1 and PTL 2 disclose herbicidal compositions containing an isoxazoline derivative or its salt and a certain known herbicide, and as examples of the known herbicide, PTL 1 describes nicosulfuron, and PTL 2 describes flazasulfuron, respectively. PTL 3 discloses a herbicidal composition containing pyroxasulfone and an acetohydroxyacid synthase inhibitor, and as examples of the acetohydroxyacid synthase inhibitor, Patent Document 3 describes nicosulfuron and flazasulfuron.

However, it is not known that the herbicidal composition comprising (A) at least one member selected from the group consisting of flazasulfuron, nicosulfuron, and their salts and (B) pyroxasulfone or its salt exhibits a synergistic herbicidal effect.

CITATION LIST

Patent Literature

PTL 1: WO-A-2004-014138
PTL 2: WO-A-2008-075743
PTL 3: WO-A-2009-112454

SUMMARY OF INVENTION

Technical Problem

At present, a large number of herbicidal compositions have been developed and used. However, weeds to be controlled include a lot of kinds, and the emergence thereof extends over a long period of time. Therefore, the appearance of a herbicidal composition having a broad weed spectrum and having a high activity and a long residual effect is desired.

Solution to Problem

By combining (A) at least one member selected from the group consisting of flazasulfuron, nicosulfuron, and their salts and (B) pyroxasulfone or its salt, a herbicidal composition having a broad weed spectrum and having a high activity and a long residual effect can be provided.

Specifically, the present invention relates to a synergistic herbicidal composition comprising (A) at least one member selected from the group consisting of flazasulfuron, nicosulfuron, and their salts (hereinafter abbreviated as "Compound A") and (B) pyroxasulfone or its salt (hereinafter abbreviated as "Compound B"). In addition, the present invention relates to a method of controlling weeds or inhibiting the growth thereof by applying an effective amount of the foregoing synergistic herbicidal composition to weeds or a place where they grow. Furthermore, the present invention relates to a method of controlling weeds or inhibiting the growth thereof by applying synergistic herbicidally effective amounts of Compound A and Compound B to weeds or a place where they grow.

Advantageous Effects of Invention

According to the present invention, a herbicidal composition which has a broad weed spectrum, has a high activity, is reduced in an application amount of a herbicidal ingredient, and has a long residual effect can be provided.

When the herbicidal activity in a case where two active ingredients are combined, is larger than the simple sum of the respective herbicidal activities of the two active ingredients (the expected activity), it is called a synergistic effect. The activity expected by the combination of two active ingredients can be calculated as follows (Colby S. R., "Weed", vol. 15, p. 20-22, 1967).

$$E = \alpha + \beta - (\alpha \times \beta \div 100)$$

where
$\alpha$: growth inhibition rate when treated with x(g/ha) of herbicide X,
$\beta$: growth inhibition rate when treated with y(g/ha) of herbicide Y,
E: growth inhibition rate expected when treated with x(g/ha) of herbicide X and y (g/ha) of herbicide Y.

That is, when the actual growth inhibition rate (measured value) is larger than the growth inhibition rate by the above calculation (calculated value), the activity by the combination can be regarded as showing a synergistic effect. The herbicidal composition of the present invention shows a synergistic effect when calculated by the above formula.

DESCRIPTION OF EMBODIMENTS

As for Compound A, flazasulfuron (common name) is 1-(4,6-dimethoxypyrimidin-2-yl)-3-(3-trifluoromethyl-2-pyridylsulfony)urea, and nicosulfuron (common name) is 2-(4,6-dimethoxypyrimidin-2-ylcarbamoylsulfamoyl)-N,N-dimethylnicotinamide.

As for Compound B, pyroxasulfone (common name) is 3-[5-(difluoromethoxy)-1-methyl-3-(trifluoromethyl)pyrazol-4-ylmethylsulfonyl]-4,5-dihydro-5,5-dimethyl-1,2-oxazole.

The salt included in Compound A and Compound B may be any salt so long as it is agriculturally acceptable. Examples thereof include alkali metal salts such as a sodium salt and a potassium salt; alkaline earth metal salts such as a magnesium salt and a calcium salt; ammonium salts such as a monomethylammonium salt, a dimethylammonium salt and a triethylammonium salt; inorganic acid salts such as a hydrochloride, a perchlorate, a sulfate and a nitrate, and organic acid salts such as an acetate and a methanesulfonate.

A mixing ratio of Compound A to Compound B must be properly adjusted depending upon the formulation form, the weather condition, the type and growth state of the weed to be controlled, and the like and cannot be unequivocally defined. However, for example, it is from 27:1 to 1:50, preferably from 15:1 to 1:40, and more preferably from 8:1 to 1:30 in terms of a Compound A:Compound B weight ratio.

In the case where Compound A is flazasulfuron, a mixing ratio of flazasulfuron to Compound B is, for example, from 27:1 to 1:50, preferably from 15:1 to 1:40, and more preferably from 8:1 to 1:30 in terms of a Compound A:Compound B weight ratio. When flazasulfuron and pyroxasulfone are mixed in the above ratio of from 8:1 to 1:30, an especially excellent effect (for example, a synergistic herbicidal effect) is exhibited as compared with other mixing ratios.

In the case where Compound A is nicosulfuron, a mixing ratio of nicosulfuron to Compound B is, for example, from 15:1 to 1:50, preferably from 4:1 to 1:30, and more preferably from 2:1 to 1:15 in teiuis of a Compound A:Compound B weight ratio. When nicosulfuron and pyroxasulfone are mixed in the above ratio of from 2:1 to 1:15, an especially excellent effect (for example, a synergistic herbicidal effect) is exhibited as compared with other mixing ratios.

An application amount of each of Compound A and Compound B must be properly adjusted depending upon the mixing ratio of Compound A to Compound B, the formulation form, the weather condition, the type and growth state of the weed to be controlled, and the like and cannot be unequivocally defined. However, for example, the application amount of Compound A is from 10 to 300 g/ha, preferably from 10 to 200 g/ha, and more preferably from 10 to 100 g/ha; and the application amount of Compound B is from 7.5 to 500 g/ha, preferably from 10 to 450 g/ha, and more preferably from 12.5 to 300 g/ha.

In the case where Compound A is flazasulfuron, the application amount of Compound A is from 10 to 200 g/ha, preferably from 10 to 150 g/ha, and more preferably from 10 to 100 g/ha; and the application amount of Compound B is from 7.5 to 500 g/ha, preferably from 10 to 400 g/ha, and more preferably from 12.5 to 300 g/ha.

In the case where Compound A is nicosulfuron, the application amount of Compound A is from 10 to 300 g/ha, preferably from 15 to 200 g/ha, and more preferably from 20 to 100 g/ha; and the application amount of Compound B is from 20 to 500 g/ha, preferably from 50 to 450 g/ha, and more preferably from 50 to 300 g/ha.

The herbicidal composition of the present invention may be applied to weeds or may be applied to a place where they grow. Further, it may be applied at any time either before or after the emergence of the weeds. Further, the herbicidal composition of the present invention may take various application forms such as soil application, foliar application, irrigation application, and submerged application, and it can be applied to agricultural fields such as upland fields, orchards and paddy fields, and non-cropland such as ridges of fields, fallow fields, play grounds, golf courses, vacant lands, forests, factory sites, railway sides and roadsides.

The herbicidal composition of the present invention can control a broad range of weeds such as annual weeds and perennial weeds. The weeds to be controlled by the herbicidal composition of the present invention may, for example, be cyperaceae such as green kyllinga (*Cyperus brevifolia* var. *leiolepis*), purple nutsedge (*Cyperus rotundus* L.), yellow nutsedge (*Cyperus esculentus* L.), or amur cyperus (*Cyperus microiria* Steud.); gramineae such as barnyardgrass (*Echinochloa crus-galli* L., *Echinochloa oryzicola* vasing.), crabgrass (*Digitaria sanguinalis* (L). Scop., *Digitaria ischaemum* Muhl., *Digitaria adscendens* Henr., *Digitaria microbachne* Henr., *Digitaria horizontalis* Willd.), green foxtail (*Setaria viridis* L.), goosegrass (*Eleusine indica* L.), johnsongrass (*Sorghum halepense* L.), annual bluegrass (*Poa annua* L.), panic grass (*Panicum* spp.) guinea grass (*Panicum maximum* Jacq.), marmeladegrass or signal grass (*Brachiaria* spp.), surinam grass (*Brachiaria decumbens* Stapf), *paspalum* (*Paspalum* spp.), itchgrass (*Rottboellia cochinchinensis* (LOUR.) W.D.CLAYTON), or wild oat (*Avena fatua* L.); scrophulariaceae such as persian speedwell (*Veronica persica* Poir.), or corn speedwell (*Veronica arvensis* L.); compositae such as beggar ticks (*Bidens* spp.), hairy fleabane (*Conyza bonariensis* (L.) Cronq.), horseweed (*Erigeron canadensis* L.), dandelion (*Taraxacum officinale* Weber), or common cocklebur (*Xanthium strumarium* L.); *leguminosae* such as white clover (*Trifolium repens* L.); caryophyllaceae such as sticky chickweed (*Cerastium glomeratum* Thuill.), or common chickweed (*Stellaria media* L.); euphorbiaceae such as garden spurge (*Euphorbia hirta* L.), or threeseeded copperleaf (*Acalypha australis* L.); plantaginaceae such as asiatic plantain (*Plantago asiatica* L.); oxalidaceae such as creeping woodsorrel (*Oxalis corniculata* L.); apiaceae such as lawn pennywort (*Hydrocotyle sibthorpioides* Lam.); violaceae such as violet (*Viola mandshurica* W. Becker); iridaceae such as blue-eyedgrass (*Sisyrinchium rosulatum* Bicknell); geraniaceae such as carolina geranium (*Geranium carolinianum* L.); labiatae such as purple deadnettle (*Lamium purpureum* L.), or henbit (*Lamium amplexicaule* L.); malvaceae such as velvetleaf (*Abutilon theophrasti* MEDIC.), or prickly sida (*Sida spinosa* L.); convolvulaceae such as tall morningglory (*Ipomoea purpurea* L.), or field bindweed (*Convolvulus arvensis* L.); chenopodiaceae such as common lambsquarters (*Chenopodium album* L.); portulacaceae such as common purslane (*Portulaca oleracea* L.); amaranthaceae such as redroot pigweed (*Amaranthus retroflexus* L.); solanaceae such as black nightshade (*Solanum nigrum* L.); polygonaceeae such as spotted knotweed (*Polygonum lapathifolium* L.), or green smartweed (*Polygonum scabrum* MOENCH); cruciferae such as flexuous bittercress (*Cardamine flexuosa* WITH.).

The herbicidal composition of the present invention has advantages such as exhibiting a high control effect on, for example, perennial gramineae such as johnsongrass or paspalum; cyperaceae such as green kyllinga, purple nutsedge, yellow nutsedge or amur cyperus; or inhibiting the growth of weeds for a long time.

The herbicidal composition of the present invention may further contain one or more other herbicidal compounds in addition to the above-described active ingredients, and there is a case where it is thereby possible to improve e.g. the range of weeds to be controlled, the timing for application of the herbicidal composition, the herbicidal activities, etc. to more desirable ways. Such other herbicidal compounds include, for example, the following compounds (common names and the like by ISO, or test codes, here, "under application for approval by ISO" means common), and one or more of them may suitably be selected for use. Even when not specifically mentioned here, in a case where such compounds have salts, alkyl esters, hydrates, different crystal forms, various structural isomers, etc., they are, of course, all included.

(1) Those which are believed to exhibit herbicidal effects by disturbing hormone activities of plants, such as a phenoxy type such as 2,4-D, 2,4-D-butotyl, 2,4-D-butyl, 2,4-D-dimethylammonium, 2,4-D-diolamine, 2,4-D-ethyl, 2,4-D-2-ethylhexyl, 2,4-D-isobutyl, 2,4-D-isoctyl, 2,4-D-isopropyl, 2,4-D-isopropylammonium, 2,4-D-sodium, 2,4-D-isopropanolammonium, 2,4-D-trolamine, 2,4-DB, 2,4-DB-butyl, 2,4-DB-dimethylammonium, 2,4-DB-isoctyl, 2,4-DB-potassium, 2,4-DB-sodium, dichlorprop, dichlorprop-butotyl, dichlorprop-dimethylammonium, dichlorprop-isoctyl, dichlorprop-potassium, dichlorprop-P, dichlorprop-P-dimethylammonium, dichlorprop-P-potassium, dichlorprop-P-sodium, MCPA, MCPA-butotyl, MCPA-dimethylammonium, MCPA-2-ethylhexyl, MCPA-potassium, MCPA-sodium, MCPA-thioethyl, MCPB, MCPB-ethyl, MCPB-sodium, mecoprop, mecoprop-butotyl, mecoprop-sodium, mecoprop-P, mecoprop-P-butotyl, mecoprop-P-dimethylammonium, mecoprop-P-2-ethylhexyl, mecoprop-P-potassium, naproanilide or clomeprop; an aromatic carboxylic acid type such as 2,3,6-TBA, dicamba, dicamba-butotyl, dicamba-diglycolamine, dicamba-dimethylammonium, dicamba-diolamine, dicamba-isopropylammonium, dicamba-potassium, dicamba-sodium, dichlobenil, picloram, picloram-dimethylammonium, picloram-isoctyl, picloram-potassium, picloram-triisopropanolammonium, picloram-triisopropylammonium, picloram-trolamine, triclopyr, triclopyr-butotyl, triclopyr-triethylammonium, clopyralid, clopyralid-olamine, clopyralid-potassium, clopyralid-triisopropanolammonium or aminopyralid; and others such as naptalam, naptalam-sodium, benazolin, benazolin-ethyl, quinclorac, quinmerac, diflufenzopyr, diflufenzopyr-sodium, fluroxypyr, fluroxypyr-2-butoxy-1-methylethyl, fluroxypyr-meptyl, chlorflurenol, chlorflurenol-methyl, aminocyclopyrachlor, aminocyclopyrachlor-methyl or aminocyclopyrachlor-potassium.

(2) Those which are believed to exhibit herbicidal effects by inhibiting photosynthesis of plants, such as a urea type such as chlorotoluron, diuron, fluometuron, linuron, isoproturon, metobenzuron, tebuthiuron, dimefuron, isouron, karbutilate, methabenzthiazuron, metoxuron, monolinuron, neburon, siduron, terbumeton, trietazine or metobromuron; a triazine type such as simazine, atrazine, atratone, simetryn, prometryn, dimethametryn, hexazinone, metribuzin, terbuthylazine, cyanazine, ametryn, cybutryne, triaziflam, indaziflam, terbutryn, propazine, metamitron or prometon; a uracil type such as bromacil, bromacyl-lithium, lenacil or terbacil; an anilide type such as propanil or cypromid; a carbamate type such as swep, desmedipham or phenmedipham; a hydroxybenzonitrile type such as bromoxynil, bromoxynil-octanoate, bromoxynil-heptanoate, ioxynil, ioxynil-octanoate, ioxynil-potassium or ioxynil-sodium; and others such as pyridate, bentazone, bentazone-sodium, amicarbazone, methazole or pentanochlor.

(3) Quaternary ammonium salt type such as paraquat or diquat, which is believed to be converted to free radicals by itself to form active oxygen in the plant body and shows rapid herbicidal efficacy.

(4) Those which are believed to exhibit herbicidal effects by inhibiting chlorophyll biosynthesis of plants and abnormally accumulating a photosensitizing peroxide substance in the plant body, such as a diphenylether type such as nitrofen, chlomethoxyfen, bifenox, acifluorfen, acifluorfen-sodium, fomesafen, fomesafen-sodium, oxyfluorfen, lactofen, aclonifen, ethoxyfen-ethyl (HC-252), fluoroglycofen-ethyl or fluoroglycofen; a cyclic imide type such as chlorphthalim, flumioxazin, flumiclorac, flumiclorac-pentyl, cinidon-ethyl, fluthiacet or fluthiacet-methyl; and others such as oxadiargyl, oxadiazon, sulfentrazone, carfentrazone-ethyl, thidiazimin, pentoxazone, azafenidin, isopropazole, pyraflufen-ethyl, benzfendizone, butafenacil, saflufenacil, flupoxam, fluazolate, profluazol, pyraclonil, flufenpyr-ethyl, bencarbazone, ethyl[3-(2-chloro-4-fluoro-5-(3-methyl-2,6-dioxo-4-trifluoromethyl-3,6-dihydro-2H-pyrimidin-1-yl)phenoxy)pyridin-2-yloxy]acetate (SYN-523).

(5) Those which are believed to exhibit herbicidal effects characterized by bleaching activities by inhibiting chromogenesis of plants such as carotenoids, such as a pyridazinone type such as norflurazon, chloridazon or metflurazon; a pyrazole type such as pyrazolynate, pyrazoxyfen, benzofenap, topramezone or pyrasulfotole; and others such as amitrole, fluridone, flurtamone, diflufenican, methoxyphenone, clomazone, sulcotrione, mesotrione, tembotrione, tefuryltrione (AVH-301), bicyclopyrone, isoxaflutole, difenzoquat, difenzoquat-metilsulfate, isoxachlortole, benzobicyclon, picolinafen or beflubutamid.

(6) Those which exhibit strong herbicidal effects specifically to gramineous plants, such as an aryloxyphenoxypropionic acid type such as diclofop-methyl, diclofop, pyriphenop-sodium, fluazifop-butyl, fluazifop, fluazifop-P, fluazifop-P-butyl, haloxyfop-methyl, haloxyfop, haloxyfop-etotyl, haloxyfop-P, haloxyfop-P-methyl, quizalofop-ethyl, quizalofop-P, quizalofop-P-ethyl, quizalofop-P-tefuryl, cyhalofop-butyl, fenoxaprop-ethyl, fenoxaprop-P, fenoxaprop-P-ethyl, metamifop-propyl, metamifop, clodinafop-propargyl, clodinafop or propaquizafop; a cyclohexanedione type such as alloxydim-sodium, alloxydim, clethodim, sethoxydim, tralkoxydim, butroxydim, tepraloxydim, profoxydim or cycloxydim; and others such as flamprop-M-methyl, flamprop-M or flamprop-M-isopropyl.

(7) Those which are believed to exhibit herbicidal effects by inhibiting an amino acid biosynthesis of plants, such as a sulfonylurea type such as chlorimuron-ethyl, chlorimuron, sulfometuron-methyl, sulfometuron, primisulfuron-methyl, primisulfuron, bensulfuron-methyl, bensulfuron, chlorsulfuron, metsulfuron-methyl, metsulfuron, cinosulfuron, pyrazosulfuron-ethyl, pyrazosulfuron, azimsulfuron, flazasulfuron, rimsulfuron, nicosulfuron, imazosulfuron, cyclosulfamuron, prosulfuron, flupyrsulfuron-methyl-sodium, flupyrsulfuron, triflusulfuron-methyl, triflusulfuron, halosulfuron-methyl, halosulfuron, thifensulfuron-methyl, thifensulfuron, ethoxysulfuron, oxasulfuron, ethametsulfuron, ethametsulfuron-methyl, iodosulfuron, iodosulfuron-methyl-sodium, sulfosulfuron, triasulfuron, tribenuron-methyl, tribenuron, tritosulfuron, foramsulfuron, trifloxysulfuron, trifloxysulfuron-sodium, mesosulfuron-methyl, mesosulfuron, orthosulfamuron, flucetosulfuron, amidosulfuron, propyrisulfuron (TH-547), metazosulfuron, or a compound disclosed in the claim of WO2005092104; a triazolopyrimidinesulfonamide type such as flumetsulam, metosulam, diclosulam, cloransulam-methyl, florasulam, penoxsulam or pyroxsulam; an imidazolinone type such as imazapyr, imazapyr-isopropylammonium, imazethapyr, imazethapyr-ammonium, imazaquin, imazaquin-ammonium, imazamox, imazamox-ammonium, imazamethabenz, imazamethabenz-methyl or imazapic; a pyrimidinylsalicylic acid type such as pyrithiobac-sodium, bispyribac-sodium, pyriminobac-methyl, pyribenzoxim, pyriftalid or pyrimisulfan; a sulfonylaminocarbonyltriazolinone type such as flucarbazone, flucarbazone-sodium, propoxycarbazone-sodium, propoxycarbazone or thiencarbazone; and others such as glyphosate, glyphosate-sodium, glyphosate-potassium, glyphosate-ammonium, glyphosate-diammonium, glyphosate-isopropylammonium, glyphosate-trimesium, glyphosate-sesquisodium, glufosinate, glufosinate-ammonium, glufosinate-P, glufosinate-P-ammonium, glufosinate-P-sodium, bilanafos, bilanafos-sodium or cinmethylin.

(8) Those which are believed to exhibit herbicidal effects by inhibiting cell mitoses of plants, such as a dinitroaniline type such as trifluralin, oryzalin, nitralin, pendimethalin, ethalfluralin, benfluralin, prodiamine, butralin or dinitramine; an amide type such as bensulide, napropamide, propyzamide or pronamide; an organic phosphorus type such as amiprofos-methyl, butamifos, anilofos or piperophos; a phenyl carbamate type such as propham, chlorpropham, barban or carbetamide; a cumylamine type such as daimuron, cumyluron, bromobutide or methyldymron; and others such as asulam, asulam-sodium, dithiopyr, thiazopyr, chlorthal-dimethyl, chlorthal or diphenamid.

(9) Those which are believed to exhibit herbicidal effects by inhibiting protein biosynthesis or lipid biosynthesis of plants, such as a chloroacetamide type such as alachlor, metazachlor, butachlor, pretilachlor, metolachlor, S-metolachlor, thenylchlor, pethoxamid, acetochlor, propachlor, dimethenamid, dimethenamid-P, propisochlor or dimethachlor; a thiocarbamate type such as molinate, dimepiperate, pyributicarb, EPTC, butylate, vernolate, pebulate, cycloate, prosulfocarb, esprocarb, thiobencarb, diallate, tri-allate or orbencarb; and others such as etobenzanid, mefenacet, flufenacet, tridiphane, cafenstrole, fentrazamide, oxaziclomefone, indanofan, benfuresate, fenoxasulfone, dalapon, dalapon-sodium, TCA-sodium or trichloroacetic acid.

(10) MSMA, DSMA, CMA, endothall, endothall-dipotassium, endothall-sodium, endothall-mono(N,N-dimethylalkylammonium), ethofumesate, sodium chlorate, pelargonic acid (nonanoic acid), fosamine, fosamine-ammonium, pinoxaden, ipfencarbazone (HOK-201), aclolein, ammonium sulfamate, borax, chloroacetic acid, sodium chloroacete, cyanamide, methylarsonic acid, dimethylarsinic acid, sodium dimethylarsinate, dinoterb, dinoterb-ammonium, dinoterb-diolamine, dinoterb-acetate, DNOC, ferrous sulfate, flupropanate, flupropanate-sodium, isoxaben, mefluidide, mefluidide-diolamine, metam, metam-ammonium, metam-potassium, metam-sodium, methyl isothiocyanate, pentachlorophenol, sodium pentachlorophenoxide, pentachlorophenol laurate, quinoclamine, sulfuric acid, urea sulfate, methiozolin (MRC-01), etc.

(11) Those which are believed to exhibit herbicidal effects by being parasitic on plants, such as *Xanthomonas campestris, Epicoccosirus nematosorus, Epicoccosirus nematosperus, Exserohilum monoseras* or *Drechsrela monoceras*.

The herbicidal composition of the present invention may be prepared by mixing Compound A and Compound B, as active ingredients, with various agricultural additives in accordance with conventional formulation methods for agricultural chemicals, and applied in various formulations such as dusts, granules, water dispersible granules, wettable powders; tablets, pills, capsules (including a formulation packaged by a water soluble film), water-based suspensions, oil-based suspensions, microemulsions, suspoemulsions, water soluble powders, emulsifiable concentrates, soluble concentrates or pastes. It may be formed into any formulation which is commonly used in this field, so long as the object of the present invention is thereby met.

At the time of the formulation, Compound A and Compound B may be mixed together for the formulation, or they may be separately formulated and then mixed for application.

The additives to be used for the formulation include, for example, a solid carrier such as kaolinite, sericite, diatomaceous earth, slaked lime, calcium carbonate, talc, white carbon, kaoline, bentonite, clay, sodium carbonate, sodium bicarbonate, mirabilite, zeolite or starch; a solvent such as water, toluene, xylene, solvent naphtha, dioxane, dimethylsulfoxide, N,N-dimethylformamide, dimethylacetamide, N-methyl-2-pyrrolidone or an alcohol; an anionic surfactant such as a salt of fatty acid, a benzoate, a polycarboxylate, a salt of alkylsulfuric acid ester, an alkyl sulfate, an alkylaryl sulfate, an alkyl diglycol ether sulfate, a salt of alcohol sulfuric acid ester, an alkyl sulfonate, an alkylaryl sulfonate, an aryl sulfonate, a lignin sulfonate, an alkyldiphenylether disulfonate, a polystyrene sulfonate, a salt of alkylphosphoric acid ester, an alkylaryl phosphate, a styrylaryl phosphate, a salt of polyoxyethylene alkyl ether sulfuric acid ester, a polyoxyethylene alkylaryl ether sulfate, a salt of polyoxyethylene alkylaryl ether sulfuric acid ester, a polyoxyethylene alkyl ether phosphate, a salt of polyoxyethylene alkylaryl phosphoric acid ester, a salt of polyoxyethylene aryl ether phosphoric acid ester, a naphthalene sulfonic acid condensed with formaldehyde or a salt of alkylnaphthalene sulfonic acid condensed with formaldehyde; a nonionic surfactant such as a sorbitan fatty acid ester, a glycerin fatty acid ester, a fatty acid polyglyceride, a fatty acid alcohol polyglycol ether, acetylene glycol, acetylene alcohol, an oxyalkylene block polymer, a polyoxyethylene alkyl ether, a polyoxyethylene alkylaryl ether, a polyoxyethylene styrylaryl ether, a polyoxyethylene glycol alkyl ether, polyethylene glycol, a polyoxyethylene fatty acid ester, a polyoxyethylene sorbitan fatty acid ester, a polyoxyethylene glycerin fatty acid ester, a polyoxyethylene hydrogenated castor oil or a polyoxypropylene fatty acid ester; and a vegetable oil or mineral oil such as olive oil, kapok oil, castor oil, palm oil, camellia oil, coconut oil, sesame oil, corn oil, rice bran oil, peanut oil, cottonseed oil, soybean oil, rapeseed oil, linseed oil, tung oil or liquid paraffins. These additives may suitably be selected for use alone or in combination as a mixture of two or more of them, so long as the object of the present invention is met. Further, additives other than the above-mentioned may be suitably selected for use among those known in this field. For example, various additives commonly used, such as a filler, a thickener, an anti-settling agent, an anti-freezing agent, a dispersion stabilizer, a safener, an anti-mold agent, a bubble agent, a disintegrator and a binder, may be used. The mix ratio by weight of the active ingredient to such various additives of the herbicidal composition of the present invention may be from 0.001:99.999 to 95:5, preferably from 0.005:99.995 to 90:10.

As a method of applying the herbicidal composition of the present invention, a proper method can be employed among various methods depending upon various conditions such as the application site, the type of the formulation, and the type and the growth stage of the noxious plants to be controlled, and for example, the following methods may be mentioned.

1. Compound A and Compound B are formulated together, and the formulation is applied as it is.

2. Compound A and Compound B are formulated together, the formulation is diluted to a predetermined concentration with e.g. water, and as the case requires, a spreader (such as a surfactant, a vegetable oil or a mineral oil) is added for application.

3. Compound A and Compound B are separately formulated and applied as they are.

4. Compound A and Compound B are separately formulated, and they are diluted to a predetermined concentration with e.g. water, and as the case requires, a spreader (such as a surfactant, a vegetable oil or a mineral oil) is added for application, respectively.

5. Compound A and Compound B are separately formulated, and the formulations are mixed when diluted to a predetermined concentration with e.g. water, and as the case requires, a spreader (such as a surfactant, a vegetable oil or a mineral oil) is added for application.

Preferred embodiments of the present invention are hereunder described, but it should not be construed that the present invention is limited thereto.

(1) A synergistic herbicidal composition comprising (A) flazasulfuron or its salt and (B) pyroxasulfone or its salt.

(2) The composition as set forth above in (1), wherein a mixing ratio of (A) flazasulfuron or its salt to (B) pyroxasulfone or its salt is from 27:1 to 1:50 in terms of a (A):(B) weight ratio.

(3) The composition as set forth above in (1), wherein a mixing ratio of (A) flazasulfuron or its salt to (B) pyroxasulfone or its salt is from 15:1 to 1:20 in terms of a (A):(B) weight ratio.

(4) The composition as set forth above in (1), wherein a mixing ratio of (A) flazasulfuron or its salt to (B) pyroxasulfone or its salt is from 8:1 to 1:12 in terms of a (A):(B) weight ratio.

(5) A method of controlling an undesirable plant or inhibiting the growth thereof, comprising applying an effective amount of a synergistic herbicidal composition containing (A) flazasulfuron or its salt and (B) pyroxasulfone or its salt to an undesirable plant or a place where it grows.

(6) A method of controlling an undesirable plant or inhibiting the growth thereof, comprising applying synergistic herbicidally effective amounts of (A) flazasulfuron or its salt and (B) pyroxasulfone or its salt to an undesirable plant or a place where it grows.

(7) The method as set forth above in (5) or (6), wherein (A) flazasulfuron or its salt is applied in an amount of from 10 to 200 g/ha, and (B) pyroxasulfone or its salt is applied in an amount of from 7.5 to 500 g/ha.

(8) The method as set forth above in (5) or (6), wherein (A) flazasulfuron or its salt is applied in an amount of from 20 to 150 g/ha, and (B) pyroxasulfone or its salt is applied in an amount of from 10 to 400 g/ha.

(9) The method as set forth above in (5) or (6), wherein (A) flazasulfuron or its salt is applied in an amount of from 25 to 100 g/ha, and (B) pyroxasulfone or its salt is applied in an amount of from 12.5 to 300 g/ha.

(10) A synergistic herbicidal composition comprising (A) nicosulfuron or its salt and (B) pyroxasulfone or its salt.

(11) The composition as set forth above in (10), wherein a mixing ratio of (A) nicosulfuron or its salt to (B) pyroxasulfone or its salt is from 15:1 to 1:50 in terms of a (A):(B) weight ratio.

(12) The composition as set forth above in (10), wherein a mixing ratio of (A) nicosulfuron or its salt to (B) pyroxasulfone or its salt is from 4:1 to 1:30 in terms of a (A):(B) weight ratio.

(13) The composition as set forth above in (10), wherein a mixing ratio of (A) nicosulfuron or its salt to (B) pyroxasulfone or its salt is from 2:1 to 1:15 in terms of a (A):(B) weight ratio.

(14) A method of controlling an undesirable plant or inhibiting the growth thereof, comprising applying an effective amount of a synergistic herbicidal composition comprising (A) nicosulfuron or its salt and (B) pyroxasulfone or its salt to an undesirable plant or a place where it grows.

(15) A method of controlling an undesirable plant or inhibiting the growth thereof, comprising applying synergistic herbicidally effective amounts of (A) nicosulfuron or its salt and (B) pyroxasulfone or its salt to an undesirable plant or a place where it grows.

(16) The method as set forth above in (14) or (15), wherein (A) nicosulfuron or its salt is applied in an amount of from 10 to 300 g/ha, and (B) pyroxasulfone or its salt is applied in an amount of from 20 to 500 g/ha.

(17) The method as set forth above in (14) or (15), wherein (A) nicosulfuron or its salt is applied in an amount of from 15 to 200 g/ha, and (B) pyroxasulfone or its salt is applied in an amount of from 50 to 450 g/ha.

(18) The method as set forth above in (14) or (15), wherein (A) nicosulfuron or its salt is applied in an amount of from 20 to 100 g/ha, and (B) pyroxasulfone or its salt is applied in an amount of from 50 to 300 g/ha.

EXAMPLES

In order to describe the present invention in more detail, Examples are described below, but it should not be construed that the present invention is limited thereto.

Test Example 1

Upland field soil was put into a 1/1,000,000-ha pot, and seeds of black nightshade (*Solanum nigrum* L.) were sown. When the black nightshade reached the 2.3 to 2.5 leaf stage, prescribed amounts of a water dispersible granules containing flazasulfuron as an active ingredient (trade name: SHIBAGEN DF, manufactured by Ishihara Sangyo Kaisha, Ltd.) and a wettable powder containing pyroxasulfone as an active ingredient were diluted with water (corresponding to 1,000 L/ha) containing 0.05% by volume of an agricultural adjuvant (trade name: KUSARINOH, manufactured by NIHON NOHYAKU Co., Ltd.) and applied for foliar treatment by a small sprayer.

On the 21st day after the treatment, the state of growth of the black nightshade was visually observed and examined, followed by evaluation according to the following evaluation criteria. A growth inhibition rate (%) (measured value) and a growth inhibition rate (%) (calculated value) as calculated according to the foregoing Colby's method are shown in Table 1.

Growth inhibition rate (%)=weed control rate of from 0% (equivalent to the non-treated plot) to 100% (complete kill)

TABLE 1

| Active Ingredient | Dose (g/ha) | Growth Inhibition Rate of Black nightshade (%) | |
|---|---|---|---|
| | | Measured Value | Calculated Value |
| flazasulfuron | 12.5 | 33 | — |
| pyroxasulfone | 25 | 20 | — |
| flazasulfuron + pyroxasulfone | 12.5 + 25 | 72 | 46 |

Test Example 2

Upland field soil was put into a 1/1,000,000-ha pot, and seeds of crabgrass (*Digitaria sanguinalis* (L.) Scop.) were sown. When the crabgrass reached the 4.0 to 4.5 leaf stage, prescribed amounts of SHIBAGEN DF (trade name) and a wettable powder containing pyroxasulfone as an active ingredient were diluted with water (corresponding to 1,000 L/ha) containing 0.05% by volume of KUSARINOH (trade name) and applied for foliar treatment by a small sprayer.

On the 21st day after the treatment, the state of growth of the crabgrass was visually observed and examined. A growth inhibition rate (%) as calculated in the same manner as that in the foregoing Test Example 1 is shown in Table 2.

TABLE 2

| Active Ingredient | Dose (g/ha) | Growth Inhibition Rate of Crabgrass (%) | |
|---|---|---|---|
| | | Measured Value | Calculated Value |
| flazasulfuron | 50 | 70 | — |
| pyroxasulfone | 25 | 0 | — |
| | 200 | 40 | — |
| flazasulfuron + pyroxasulfone | 50 + 25 | 79 | 70 |
| | 50 + 200 | 88 | 82 |

Test Example 3

Upland field soil was put into a 1/1,000,000-ha pot, and seeds of velvetleaf (*Abutilon theophrasti* Medic.) were sown. After one day, prescribed amounts of SHIBAGEN DF (trade name) and a wettable powder containing pyroxasulfone as an active ingredient were diluted with water (corresponding to 1,000 L/ha) and applied for soil treatment by a small sprayer.

On the 21st day after the treatment, the state of growth of the velvetleaf was visually observed and examined. A growth inhibition rate (%) as calculated in the same manner as that in the foregoing Test Example 1 is shown in Table 3.

TABLE 3

| Active Ingredient | Dose (g/ha) | Growth Inhibition Rate of Velvetleaf (%) | |
|---|---|---|---|
| | | Measured Value | Calculated Value |
| flazasulfuron | 50 | 94 | — |
| pyroxasulfone | 12.5 | 13 | — |
| flazasulfuron + pyroxasulfone | 50 + 12.5 | 98 | 95 |

Test Example 4

Upland field soil was put into a 1/1,000,000-ha pot, and seeds of common lambsquarters (*Chenopodium album* L.) were sown. After one day, prescribed amounts of a water-based suspension containing nicosulfuron as an active ingredient and a wettable powder containing pyroxasulfone as an active ingredient were diluted with water (corresponding to 300 L/ha) and applied for soil treatment by a small sprayer.

On the 27th day after the treatment, the state of growth of the common lambsquarters was visually observed and examined. A growth inhibition rate (%) as calculated in the same manner as that in the foregoing Test Example 1 is shown in Table 4.

TABLE 4

| Active Ingredient | Dose (g/ha) | Growth Inhibition Rate of Common lambsquarters (%) | |
|---|---|---|---|
| | | Measured Value | Calculated Value |
| nicosulfuron | 30 | 35 | — |
| pyroxasulfone | 125 | 90 | — |
| nicosulfuron + pyroxasulfone | 30 + 125 | 100 | 94 |

Test Example 5

Upland field soil was put into a 1/300,000-ha pot, and seeds of black nightshade (*Solanum nigrum* L.) were sown. After one day, prescribed amounts of SHIBAGEN DF (trade name) and a wettable powder containing pyroxasulfone as an active ingredient were diluted with water (corresponding to 1,000 L/ha) and applied for soil treatment by a small sprayer.

On the 14th day after the treatment, the state of growth of the black nightshade was visually observed and examined. A growth inhibition rate (%) as calculated in the same manner as that in the foregoing Test Example 1 is shown in Table 5.

TABLE 5

| Active Ingredient | Dose (g/ha) | Growth Inhibition Rate of Black nightshade (%) | |
|---|---|---|---|
| | | Measured Value | Calculated Value |
| flazasulfuron | 25 | 50 | — |
| | 50 | 60 | — |
| | 100 | 80 | — |
| pyroxasulfone | 50 | 20 | — |
| | 150 | 30 | — |

TABLE 5-continued

| Active Ingredient | Dose (g/ha) | Growth Inhibition Rate of Black nightshade (%) | |
|---|---|---|---|
| | | Measured Value | Calculated Value |
| | 300 | 30 | — |
| flazasulfuron + pyroxasulfone | 25 + 300 | 93 | 65 |
| | 50 + 150 | 90 | 72 |
| | 100 + 50 | 100 | 84 |

Test Example 6

Upland field soil was put into a 1/300,000-ha pot, and seeds of wild oat (*Avena fatua* L.) were sown. After one day, prescribed amounts of SHIBAGEN DF (trade name) and a wettable powder containing pyroxasulfone as an active ingredient were diluted with water (corresponding to 1,000 L/ha) and applied for soil treatment by a small sprayer.

On the 28th day after the treatment, the state of growth of the wild oat was visually observed and examined. A growth inhibition rate (%) as calculated in the same manner as that in the foregoing Test Example 1 is shown in Table 6.

TABLE 6

| Active Ingredient | Dose (g/ha) | Growth Inhibition Rate of Wild oat (%) | |
|---|---|---|---|
| | | Measured Value | Calculated Value |
| flazasulfuron | 100 | 85 | — |
| pyroxasulfone | 12.5 | 0 | — |
| flazasulfuron + pyroxasulfone | 100 + 12.5 | 90 | 85 |

Test Example 7

Upland field soil was put into a 1/300,000-ha pot, and seeds of velvetleaf (*Abutilon theophrasti* Medic.) were sown. After one day, prescribed amounts of an oil-based suspension (trade name: ONEHOPE NYUZAI, manufactured by Ishihara Sangyo Kaisha, Ltd.) containing nicosulfuron as an active ingredient and a wettable powder containing pyroxasulfone as an active ingredient were diluted with water (corresponding to 1,000 L/ha) and applied for soil treatment by a small sprayer.

On the 28th day after the treatment, the state of growth of the velvetleaf was visually observed and examined. A growth inhibition rate (%) as calculated in the same manner as that in the foregoing Test Example 1 is shown in Table 7.

TABLE 7

| Active Ingredient | Dose (g/ha) | Growth Inhibition Rate of Velvetleaf (%) | |
|---|---|---|---|
| | | Measured Value | Calculated Value |
| nicosulfuron | 20 | 0 | — |
| | 100 | 10 | — |
| pyroxasulfone | 50 | 40 | — |
| | 100 | 70 | — |
| | 300 | 80 | — |
| nicosulfuron + pyroxasulfone | 20 + 300 | 100 | 80 |
| | 100 + 50 | 70 | 46 |
| | 100 + 100 | 80 | 73 |

While the invention has been described in detail and with reference to specific embodiments thereof, it will be apparent to one skill in the art that various changes and modifications can be made therein without departing from the sprit and scope thereof.

This application is based on Japanese patent application No. 2011-140452 filed on Jun. 24, 2011, the entire contents of which are incorporated hereinto by reference. All references cited herein are incorporated in their entirety.

INDUSTRIAL APPLICABILITY

According to the present invention, a herbicidal composition having a broad weed spectrum and having a high activity and a long residual effect can be provided.

The invention claimed is:

1. A method of controlling an undesirable plant or inhibiting the growth thereof, comprising applying a synergistic herbicidal composition comprising (A) flazasulfuron or its salt and (B) pyroxasulfone or its salt, wherein a mixing ratio of (A) to (B) is from 8:1 to 1:1 in terms of a (A):(B) weight ratio, wherein the undesirable plant is black nightshade or wild oat.

2. The method according to claim 1, wherein a mixing ratio of (A) to (B) is from 4:1 to 2:1 in terms of a (A):(B) weight ratio.

3. A method of controlling an undesirable plant or inhibiting the growth thereof, comprising applying synergistic herbicidally effective amounts of (A) flazasulfuron or its salt and (B) pyroxasulfone or its salt to an undesirable plant or a place where an undesirable plant grows, wherein (A) is applied in an amount of from 100 to 150 g/ha, and (B) is applied in an amount of from 12.5 to 150 g/ha, wherein the undesirable plant is black nightshade or wild oat.

4. The method according to claim 3, wherein (A) is applied in an amount of 100 g/ha; and (B) is applied in an amount of from 25 to 50 g/ha.

* * * * *